United States Patent [19]
Tsuji

[11] Patent Number: 5,402,769
[45] Date of Patent: Apr. 4, 1995

[54] ENDOSCOPE APPARATUS WHICH TIME-SEQUENTIALLY TRANSMITS SENSOR SIGNALS WITH IMAGE SIGNALS DURING A BLANKING PERIOD

[75] Inventor: Kiyoshi Tsuji, Musashino, Japan

[73] Assignee: Olympus Optical Co., Ltd., Tokyo, Japan

[21] Appl. No.: 29,581

[22] Filed: Mar. 11, 1993

[30] Foreign Application Priority Data

Apr. 23, 1992 [JP] Japan ............................. 4-104670
Feb. 19, 1993 [JP] Japan ............................. 5-030981

[51] Int. Cl.⁶ .................................................. A61B 1/06
[52] U.S. Cl. ............................................ 128/6; 348/74
[58] Field of Search ........................... 128/4, 6, 7–10; 358/98, 91, 92, 147; 73/335.2; 354/62; 348/65, 74, 76, 476–479

[56] References Cited

U.S. PATENT DOCUMENTS

| | | | |
|---|---|---|---|
| 4,298,260 | 11/1981 | Takayama | 354/62 |
| 4,743,965 | 5/1988 | Yamada et al. | 358/91 X |
| 4,793,182 | 12/1988 | Djorup | 73/335.02 |
| 4,803,562 | 2/1989 | Eino | 358/98 |
| 4,979,035 | 12/1990 | Uehara | 358/98 |
| 4,993,405 | 2/1991 | Takamura et al. | 358/98 X |
| 4,995,396 | 2/1991 | Inaba | 128/654 |
| 5,060,632 | 10/1991 | Hibino et al. | 128/6 |
| 5,088,492 | 2/1992 | Takayama | 128/654 |

FOREIGN PATENT DOCUMENTS

| | | |
|---|---|---|
| 3231422 | 3/1984 | Germany. |
| 60-37301 | 3/1985 | Japan. |
| 60-69620 | 4/1985 | Japan. |
| 3-236825 | 10/1991 | Japan. |
| 3236825 | 1/1992 | Japan. |

Primary Examiner—Stephen R. Crow
Assistant Examiner—John Leubecker
Attorney, Agent, or Firm—Armstrong, Westerman, Hattori, McLeland & Naughton

[57] ABSTRACT

An endoscope having at the tip of its inserting section a detecting device for detecting physical or chemical changes allows transmission of signals from the detecting device without requiring a dedicated signal line for this detecting device. For example, an electronic endoscope apparatus of the type which has an inserting section extending from an operating section, includes: a detecting device for detecting physical and chemical changes, such as a humidity sensor or a gas sensor, provided at a tip of the inserting section; a notifying device for notifying of the detection results of the detecting device by, for example, displaying them through a monitor; an image-sensing device, such as a CCD, for forming an image signal having a blanking period; and a signal line. A switching device transmits the signals from the detecting means time-sequentially with and during the blanking period of the signals from the image sensing means. With this construction, an increase in the diameter of the endoscope inserting section can be avoided in spite of the provision of the detecting device.

9 Claims, 11 Drawing Sheets

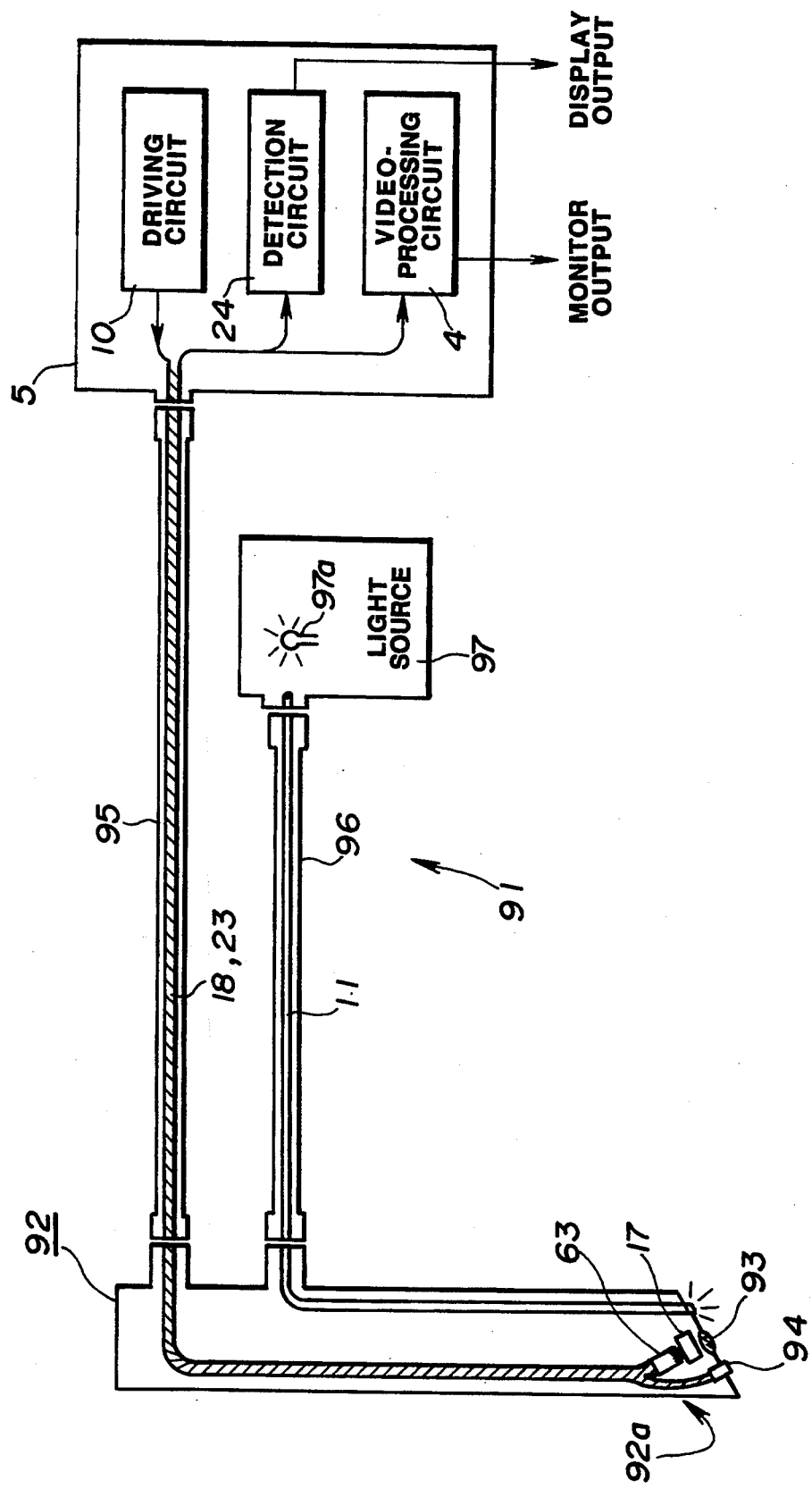

ENDOSCOPE APPARATUS WHICH TIME-SEQUENTIALLY TRANSMITS SENSOR SIGNALS WITH IMAGE SIGNALS DURING A BLANKING PERIOD

BACKGROUND OF THE INVENTION

1. Field of the Invention

This invention relates to an endoscope apparatus having at the tip of its inserting section a detection means for detecting physical or chemical changes.

2. Description of Related Art

In place of the fiber-type endoscope, which transmits optical images through an optical fiber, an electronic endoscope utilizing a photoelectric-conversion-type image sensor is beginning to find its way into the market, due to its multifunctional character. However, the electronic components inside such an electronic endoscope, including the image sensor, are rather sensitive to environmental conditions, such as temperature, humidity and disinfectant gas, so that when placed under any severe condition for a long period of time, the electronic components may become irreparably damaged.

The flexible sheathing tube of an endoscope consists of a rubber tube having a bendable structure, so that it, particularly, is subject to generation of cracks or pinholes, through which water is likely enter. Also, when sterilizing the endoscope with a disinfectant gas, intrusion of gas may occur through these cracks or pinholes, resulting in the electronic components inside the electronic endoscope, in particular, the semiconductor devices, being damaged. Further, any cracks or pinholes may allow infectious, disease-causing organisms to get into the electronic endoscope during an operation; therefore, the endoscope cannot be sufficiently sterilized by washing in antiseptic solution alone, and there is the possibility of a second patient being infected with a disease. In view of this, Japanese Patent Laid-Open No. 1991-236825 and Japanese Utility Model Laid-Open No. 1985-37301 have proposed endoscope structures according to which a humidity sensor is provided inside the endoscope, thereby detecting any leakage of water into the endoscope.

In the technical means described in Japanese Utility Model Laid-Open No. 1985-37301, in which any water leakage is detected by a humidity sensor provided in the tip section of the endoscope, the electronic components inside the electronic endoscope may become damaged to such a degree as to be irreparable by the time the sensor has detected the leakage.

In view of this, the endoscope described in Japanese Patent Laid-Open No. 1991-236825 adopts a structure in which the electronic components mounted in the electronic endoscope are collectively arranged in a waterproof structure forming an image sensor unit, with the humidity sensor being arranged on the external surface of this image sensor unit. The humidity sensor is connected to a water-leakage detecting circuit inside an endoscope controller through a dedicated signal line for leakage detection, thereby making it possible to transmit a water-leakage detection signal before the electronic components have been damaged by water leakage. With this prior-art technique, any water leakage can be repaired before the electronic components have been damaged thereby, thus enabling the image sensing unit to be used again.

However, the above-described prior-art technique has a problem in that the humidity detecting means is provided in the tip section of the endoscope, which means a dedicated signal line for humidity detection has to be separately provided. As a result, an increase in the diameter of the inserting section is inevitable as compared to that of an endoscope apparatus not equipped with such a humidity detecting means.

Apart from this, Japanese Patent Laid-Open No. 1985-69620 discloses an endoscope having a solid-state image sensing device in the tip section thereof, according to which at least one network tube is formed by a plurality of conductors which constitute outlet paths for image signals obtained by this solid-state image sensing device and inlet paths for drive signals for driving the solid-state image sensing device, with a bundle of light-guide fibers, an air/water-supply channel, or a forceps channel being inserted into this network tube. Due to this construction, the tube diameter of the inserting section is reduced as compared to that type of endoscope in which a plurality of conductors are arranged as separate channels, by the space occupied by those channels.

SUMMARY OF THE INVENTION

A first object of this invention is to provide an endoscope apparatus which is capable of detecting physical or chemical changes and transmitting a relevant detection signal without requiring an augmentation in the diameter of the endoscope inserting section.

A second object of this invention is to provide an endoscope apparatus which is capable of detecting physical or chemical changes, transmitting a relevant detection signal without requiring an augmentation in the diameter of the endoscope inserting section, and notifying of the detection result.

A third object of this invention is to provide an endoscope apparatus which is capable of detecting the humidity at the tip of the endoscope inserting section, and transmitting a relevant detection signal to the side of the apparatus operating section without requiring an increase in the diameter of the inserting section.

A fourth object of this invention is to provide an endoscope apparatus which can detect humidity in a reliable manner.

A fifth object of this invention is to provide an endoscope apparatus which can notify about the condition of the humidity intrusion or degree of water leakage in the tip section of the endoscope.

A sixth object of this invention is to provide an endoscope apparatus which can detect humidity reliably before the image sensing unit has suffered any damage by humidity or water leakage.

A seventh object of this invention is to provide an endoscope apparatus which is capable of reliably detecting humidity no matter from which direction of the image sensing unit it has intruded.

An eighth object of this invention is to provide an endoscope apparatus which can detect physical or chemical changes at the tip of the inserting section and transmit a relevant detection signal to the side of the apparatus operating section without allowing the signal to attenuate.

A ninth object of this invention is to provide an endoscope apparatus which is capable of detecting at least one of the following: temperature, pressure, gas, vital reaction or magnetism.

In summary, this invention relates to an endoscope apparatus comprising: detecting means for detecting physical or chemical changes provided at the tip of an inserting section, excluding means for observing an object of inspection; and signal transmission means for transmitting signals from the detection means which also has functions other than that of transmitting the signals from the detection means.

These objects and advantages of the present invention will become further apparent from the following detailed explanation.

BRIEF DESCRIPTION OF THE DRAWINGS

FIGS. 1 through 5 show a first embodiment of the present invention, of which:

FIG. 1 is a block diagram showing the overall construction of an endoscope apparatus;

FIG. 2 is a block diagram showing the construction of an essential part of the electric circuit of the endoscope apparatus;

FIG. 3 is a block diagram, partly consisting of a circuit diagram, showing in detail a humidity sensor and a water-leakage detecting circuit;

FIG. 4 is a plan view showing an example of the humidity-sensor structure; and

FIG. 5 is a sectional view showing another example of the humidity-sensor structure;

FIGS. 6 and 7 show a second embodiment of the present invention, of which:

FIG. 6 is a block diagram, partly consisting of a circuit diagram, illustrating in detail a humidity sensor and a water-leakage detecting circuit; and FIG. 7 is a graph showing the relationship between humidity-sensor output and humidity;

FIG. 12 is a block diagram, partially cut away, showing a rigid endoscope apparatus according to a seventh embodiment of the present invention.

DETAILED DESCRIPTION OF THE PREFERRED EMBODIMENTS

Embodiments of this invention will now be described with reference to the drawings.

Figure 1:
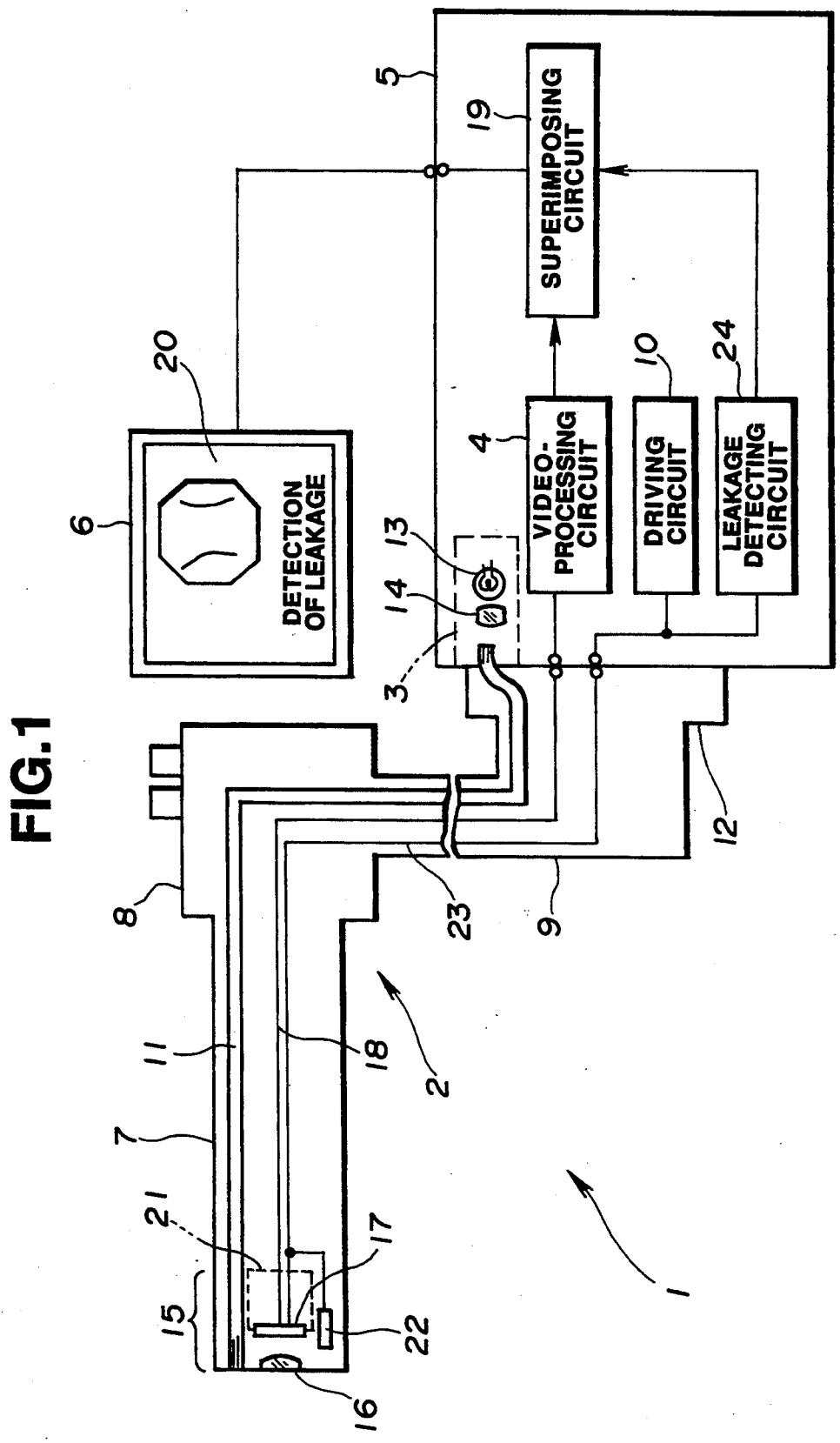
Figure 2:
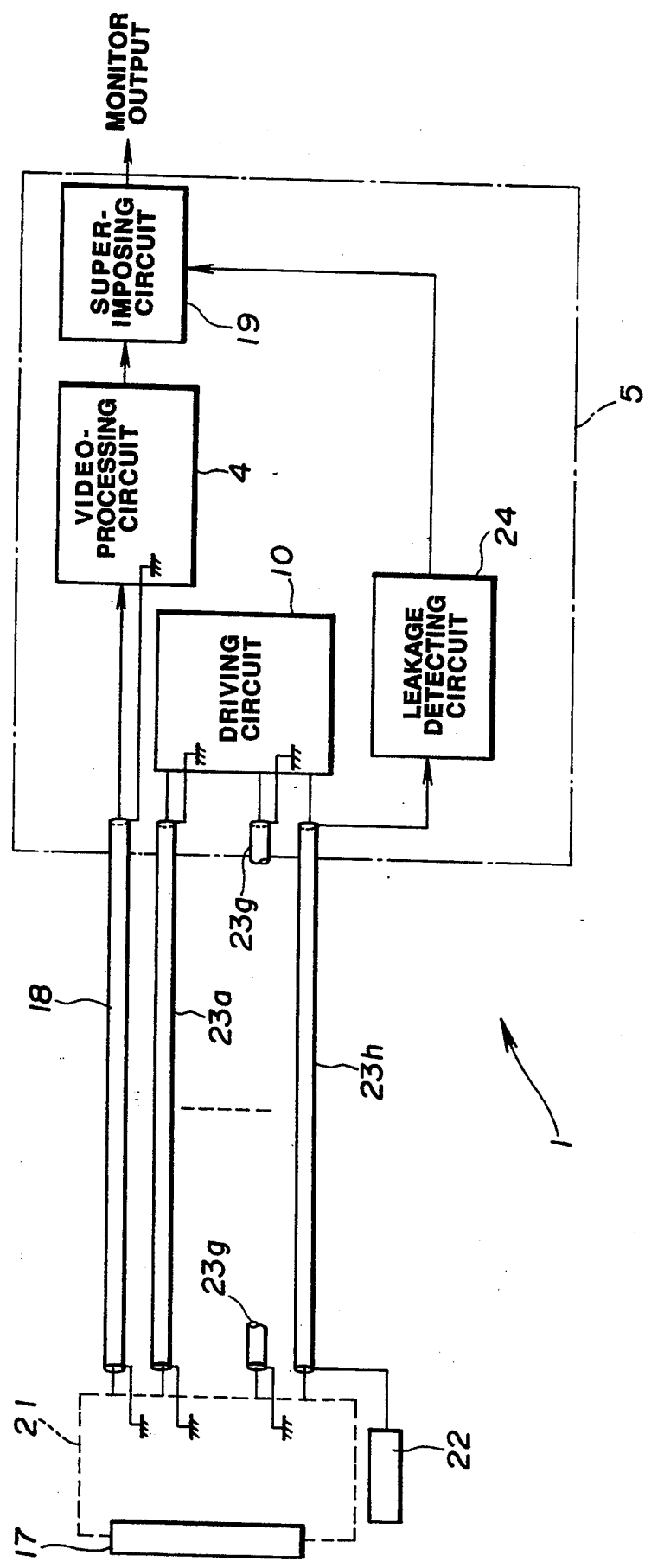
Figure 3:
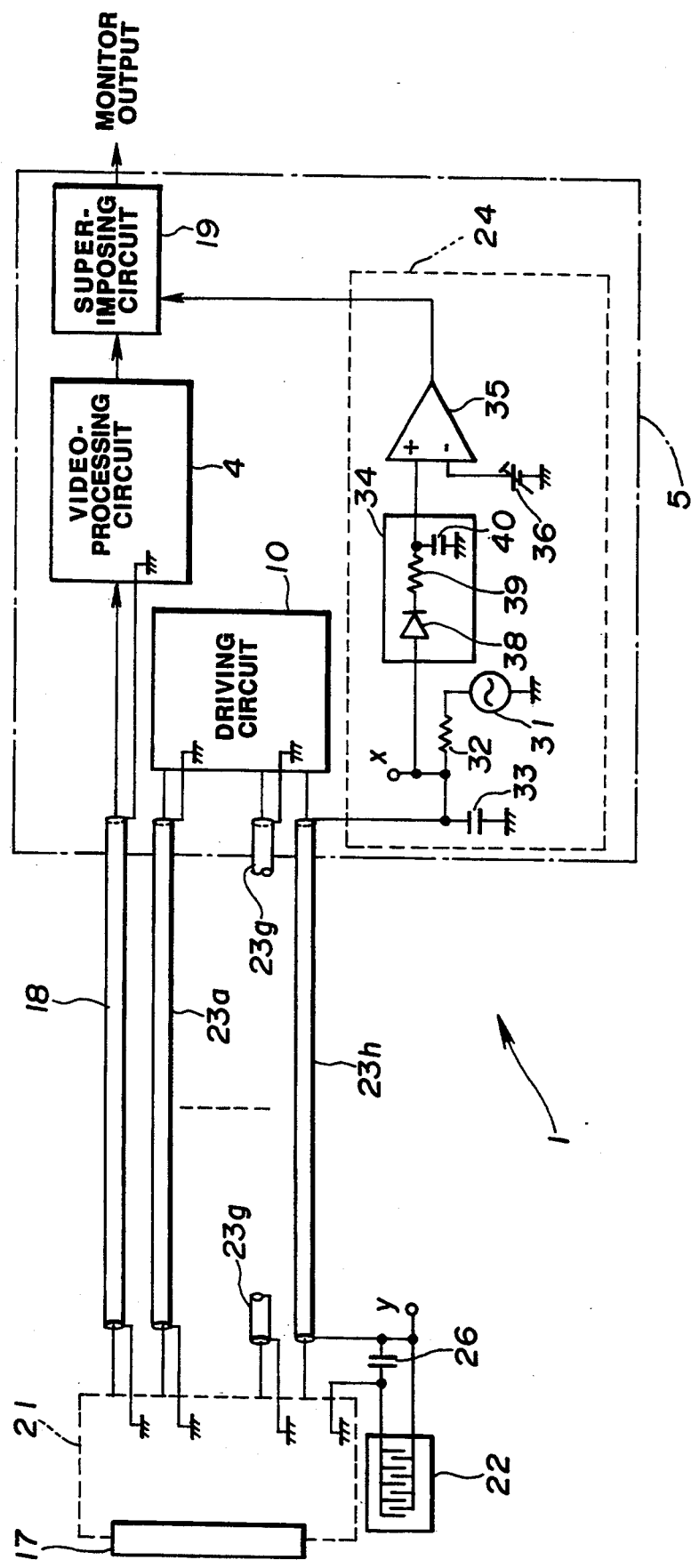
Figure 4:
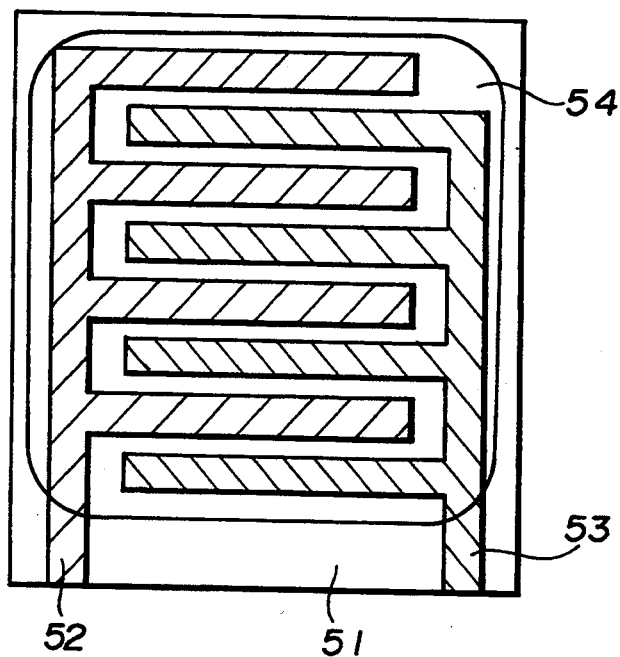
Figure 5:
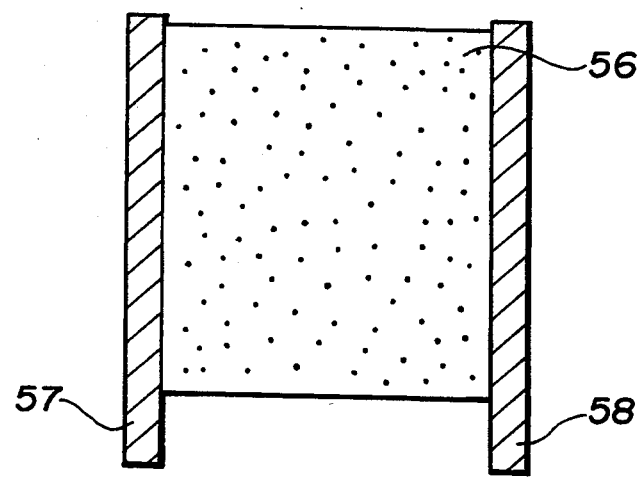

FIGS. 1 through 5 show the first embodiment of this invention, of which FIG. 1 is a block diagram showing the overall construction of an endoscope apparatus; FIG. 2 is a block diagram showing the construction of an essential part of the electric circuit of the endoscope apparatus; FIG. 3 is a block diagram, partly consisting of a circuit diagram, showing in detail a humidity sensor and a water-leakage detecting circuit; FIG. 4 is a plan view showing an example of the humidity-sensor structure; and FIG. 5 is a sectional view showing another example of the humidity-sensor structure.

As shown in FIG. 1, the main section of an endoscope apparatus 1 is composed of an endoscope 2, a light-source section 3 for supplying the endoscope 2 with illuminating light, an endoscope controller 5 containing a video-processing circuit 4 for signal processing, etc., and a monitor 6 for displaying an image of an object, etc.

The endoscope 2 is composed of a long and narrow inserting section 7, an operating section 8 formed at the rear end of the inserting section 7, and a universal cord 9 extending outwardly from the operating section 8.

Passed through the inserting section 7 and the universal cord 9 is a light guide 11 for transmitting light; by connecting a connector 12 attached to the end of the universal cord 9 to the endoscope controller 5, light is supplied form the light-source section 3.

White light emitted from a lamp 13 is condensed by a condenser lens 14 and applied to the inlet-side end surface of the light guide 11. The light is then transmitted through the light guide 11 to a tip section 15 of the endoscope 2, where it is emitted from the outlet-side end surface of the light guide to illuminate an object in front.

An optical image of the object being illuminated is formed on a solid-state image sensing device (hereinafter abbreviated as "SID") 17, such as a CCD, by an objective optical system 16 provided in the tip section 15, the SID 17 being arranged in the focal plane of this optical system. The SID 17 is covered with a leakage-proof member 21 provided inside the tip section 15.

The optical image formed on the image-forming surface of the SID 17 is photoelectrically converted by the SID 17 into an electric signal, which is transmitted to the video-processing circuit 4 through an SID-output-signal transmission cable 18, which serves as a signal line. The SID 17 is connected to a driving circuit 10 through an SID drive cable 23 which serves as a signal line. In the preferred embodiment coaxial cables or shielded cables are employed for the SID-output-signal transmission cable 18 and for the SID drive cable 23 for the purposes of reducing unnecessary radiational noise from the cables, preventing circuit malfunction due to the influence of external noises, mitigating distortion of the transmission waveform, etc.

The video-processing circuit 4 converts the electric signal into a standard video signal, which is transmitted through a superimposing circuit 19 and displayed as an object image on a screen display section 20 of the monitor 6.

Arranged in the vicinity of the leakage-proof member 21 is a humidity sensor 22 for detecting water leakage, humidity, etc. on the outside of the leakage-proof member 21. The humidity sensor 22 is connected to a leakage detecting circuit 24 in the controller 5 through the SID drive cable 23, which passes through the inserting section 7 and the universal cord 9. Based on the output of the humidity sensor 22, the leakage detecting circuit 24 outputs a detection signal indicating whether any water has been detected. This detection signal is supplied to the superimposing circuit 19, where it is superimposed on the output signal from the video-processing circuit 4 and then supplied to the monitor 6. When some water has been detected, a comment: "LEAKAGE DETECTED" or the like is displayed at the bottom on the left-hand side of the display screen of the monitor 6, or a display means (not shown) which is provided in the controller 5 gives a warning display. The leakage detection may also be notified by generating a warning sound or by simultaneously generating a visual display like a monitor display and a warning sound.

That portion of the circuit of FIG. 2 which is related to humidity detection will be described in detail with reference to FIG. 3.

Any water or humidity which has entered the tip section of the endoscope 2 is adsorbed or condensed on the surface of the humidity sensor 22, thereby changing the resistance value of the humidity sensor. The humidity sensor 22 is connected in parallel to a capacitor 26 for removing noises, one end of which capacitor is connected to a shielded conductor which is among the cables constituting the SID drive cable 23 and which is not transmitting any SID drive signal, with the other end of the capacitor 26 being grounded. As shown in FIG. 2, the SID drive cable 23 is composed of a plurality of cables 23a, . . . , 23g and 23h. The signals to be transmitted therethrough include an SID vertical drive signal, an SID horizontal drive signal, an SID power source signal, etc.

The leakage detecting circuit 24 employs an AC power source 31 as its power source, to which is connected a resistor 32 for detecting the resistance value of the humidity sensor 22 through voltage division. Because of the high impedance of the resistance value of the humidity sensor 22, the point of measurement, x, exhibits a high impedance. However, the cables in the electronic endoscope have a long length of, for example, 3 to 7 m and, in the case of medical applications, in particular, a peripheral apparatus constituting a disturbance source, such as a high-frequency knife, is used with the endoscope apparatus, so that when used under a high-impedance condition, the signal transmission line for the humidity sensor is influenced by disturbance noise, resulting in circuit malfunction. Thus, in the connecting section of the cable, it is necessary to effect impedance matching with respect to the characteristic impedance of the cable. In view of this, a capacitor 33 serving as an AC type terminator means is connected. The above-mentioned point of measurement x is connected to a rectifier-type detection circuit 34, which is composed of a diode 38, a resistor 39, and a capacitor 40 one end of which is grounded. The signal level output from the rectifier-type detection circuit 34 is compared with a reference signal level 36 by means of a comparator 35 using an operation amplifier, etc., and a signal indicating whether humidity, etc. has been detected is supplied to the superimposing circuit 19.

In this embodiment, a shielded portion of a coaxial cable is used as the transmission line for the signal from the humidity sensor 22. In the end portion of the line, the impedance condition is close to an open circuit. Thus it is desirable to avoid using the SID-output-signal transmission cable, the SID-horizontal-drive-signal transmission cable, etc., of which the impedance matching is particularly important in terms of image quality, and use another cable instead as the signal line for the humidity sensor. The driving frequency of the vertical drive signal is 15.7 (kHz), which is lower than that of the horizontal drive signal, so that even without the capacitor 26 in the endoscope tip section 15, no bad influence is generated from the viewpoint of practical use due to the terminal capacity (approximately 1000 PF) inside the SID 17, such as the CCD.

Next, examples of the structure of the humidity sensor 22 will be described with reference to FIGS. 4 and 5.

The humidity sensor shown in FIG. 4 includes an insulating substrate 51 made of polyimide, glass, ceramics, epoxy or the like, comb-like electrode patterns 52 and 53 arranged alternately on the insulating substrate 51, and a humidity-sensitive resistor coating 54 applied to these electrode patterns. The humidity-sensitive resistor coating 54 consists of a swellable high-molecular film containing a conductor material such as carbon particles or the like, and is adapted to vary the inter-electrode resistance value in accordance with the changes in the swelling condition at the time of moisture absorption and dehumidification. Even without the humidity-sensitive resistor coating 54, this humidity sensor provides a satisfactory sensitivity by increasing the pitch of the arrangement of the electrode patterns 52 and 53.

The humidity sensor shown in FIG. 5 includes a porous substrate 56, which is made of a glass, a ceramic material or the like which contains a hygroscopic electrolyte such as lithium chloride, the porous substrate 56 being placed between electrodes 57 and 58. This humidity sensor is also capable of sensing changes in electric resistance caused by moisture absorption and dehumidification.

With the first embodiment, described above, it is possible to transmit signals from a detection means provided in the tip section, such as a humidity sensor, to the side of the apparatus operating section without requiring an increase the diameter of the endoscope inserting section, and to reliably notify the operator of the detection results obtained by the detection means.

If, in the first embodiment, a temperature sensor, a pressure sensor, a gas sensor, a biosensor, a magnetometric sensor, a gravity sensor or the like is used instead of the humidity sensor, there is no need to provide a dedicated signal transmission line for such a sensor, so that the detection of physical or chemical changes by a detecting device can be effected without having to augment the diameter of the inserting section of the endoscope. In the following, the above-mentioned sensors will be described one by one.

A pressure sensor generally consists of a resistance-wire strain gage or the like. The smaller the sectional area of a metal wire having resistance, or the longer the length thereof, the larger is the resistance value thereof. Thus, when the metal wire is elongated to change its sectional area and length by applying a tension thereto, its resistance value changes, whereby the tension or pressure applied thereto can be measured. The pressure sensor structure, however, is not limited to the one described above.

A temperature sensor based, for example, on a resistance thermometer bulb utilizes the fact that the resistance value of a metal wire changes in accordance with the ambient temperature. A temperature sensor using a thermocouple detects a thermo-electromotive force at the interface between two different metals, which force changes in accordance with the ambient temperature. The construction of the temperature sensor, however, is not limited to these two types.

As regards the magnetometric sensor, there is one type based on a magnetic resistor type and another type based on a Hall element. In the former, any change in the carrier movement between electrodes on either side of a semiconductor when an electric field is applied thereto is detected as a resistance value. The latter type also utilizes the carrier movement for detect resistance value. The construction of the magnetic sensor, however, is not restricted to these two types The gas sensor functions as follows: any gas molecules adsorbed on a semiconductor surface consisting of a metal oxide cause a change in electron concentration due to electron exchange between the gas molecules and the semiconductor. This change is extracted as a change in the value of electric resistance. The construction of the gas sensor, however, is not limited to the one described above.

The biosensor has a functional film consisting of a biosubstance. When this functional film reacts with a particular chemical substance, heat is generated along with a change in ion concentration, which change is converted to an electric signal by one of the sensors described above. This biosensor is currently being used as a sensor for detecting vital reactions, for example, as an oxygen sensor or an immunity sensor utilizing antigen-antibody reactions. The construction of the biosensor, however, is not restricted to the type described above.

The gravity sensor comprises a weight which is placed on a piezoelectric element formed of quartz or ceramics sandwiched between two electrodes. The sensor is adapted to convert a change in gravity to a change in voltage. Apart from its use as an acceleration sensor, this sensor can be used in the detection of an attitude of something in a static condition (i.e., whether it is set horizontal, vertical, reversed, etc.). It may be used, for example, in the attitude control of an endoscope. The construction of the gravity sensor, however, is not limited to the one described above.

Figure 6:
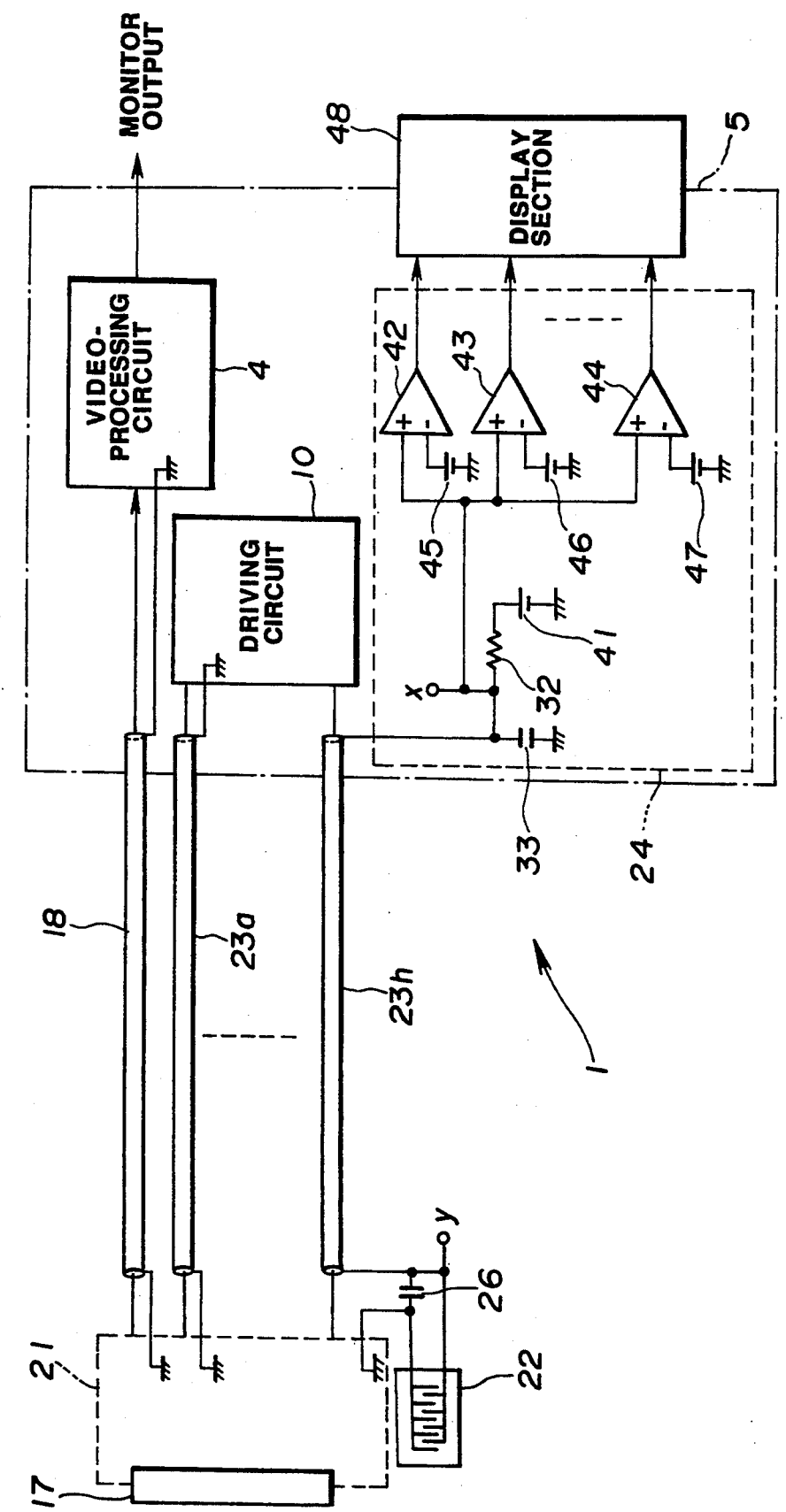
Figure 7:
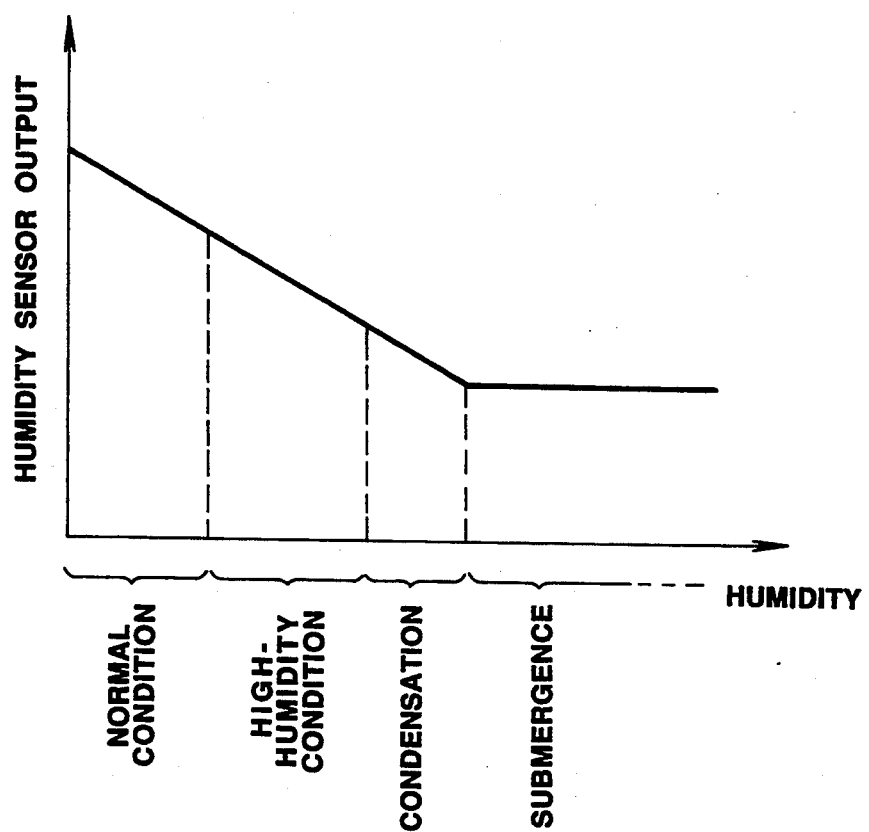

FIGS. 6 and 7 show the second embodiment of the present invention, of which FIG. 6 is a block diagram, partly consisting of a circuit diagram, illustrating in detail a humidity sensor and a water-leakage detecting circuit; and FIG. 7 is a graph showing the relationship between humidity-sensor output and humidity. The second embodiment differs from the first one, described above, in the following point:

The signal source for driving the humidity sensor is a DC power source 41. The humidity sensor output, obtained at the point of measurement x, is supplied to comparators 42, 43 and 44, where it is compared with different reference levels 45, 46 and 47. As a result, it is possible, as shown in FIG. 7, to distinguish the condition around the sensor between "normal", "high humidity", "condensation" and "submergence". The detection signals from the comparators 42, 43 and 44 are displayed in a display section 48 which is different from the monitor 6 (see FIG. 6) and which is provided in the endoscope controller 5, giving a warning to the observer.

High-accuracy discrimination is also possible when A/D converters are employed as comparators.

Figure 8:
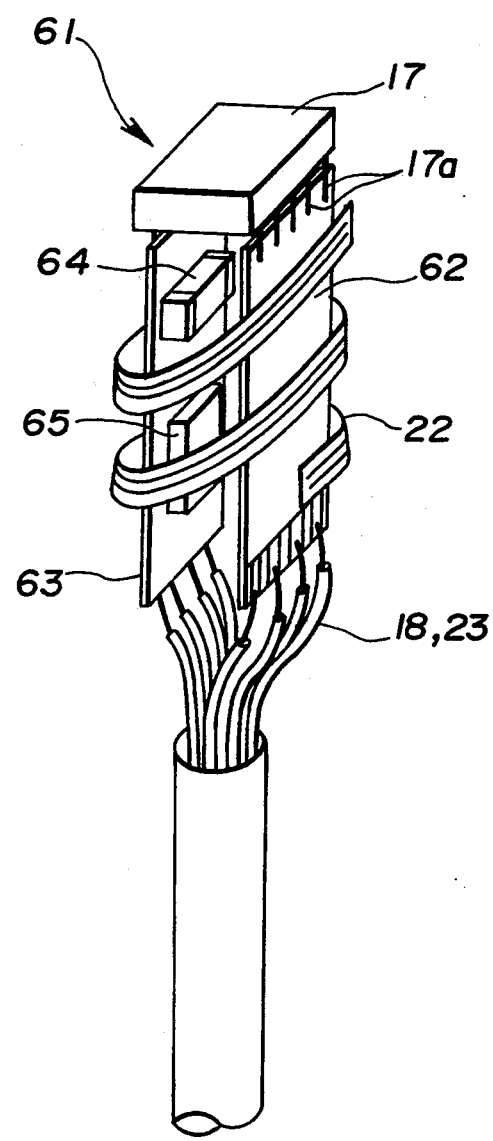
FIG. 8 is a perspective view showing a tip-section unit serving as the image sensing unit in a third embodiment of the present invention.

FIG. 8 is a perspective view showing a tip-section unit 61 serving as the image-sensing unit of the third embodiment of the present invention. Here, a description of those components of the third embodiment which are the same as those of the first and second embodiments will be omitted, and only those points which differ from the first and second embodiments will be described.

The tip-section unit 61 has a structure as shown in FIG. 8. That is, the SID 17 is electrically connected to substrates 62 and 63 through lead feet 17a protruding from that surface thereof which is on the opposite side of its image formation surface. A capacitor 64 and an IC 65, which serve to supply electric power to the SID 17, are arranged on that surface of the substrate 63 which faces the substrate 62. The IC 65 functions, for example, as a buffer for amplifying the output of the SID 17 and driving the cables, and as a generator of various bias voltages, such as the SUB voltage and the gate voltages to be supplied to the SID 17. The cables 18 and 23 are connected to the substrates 62 and 63.

A humidity sensor 22 in the form of a long and narrow strip is wound around the above-described tip-section unit 61 at a fixed pitch. This humidity sensor 22 comprises a long and narrow bendable substrate, for example, a flexible substrate, and two long and narrow electrodes arranged close to each other on this substrate. It is not the comb-like type shown in FIG. 4 but has a parallel pattern in which the electrodes are closely arranged. It is based on the same detection principle as the one described above, detecting humidity from a change in impedance caused by any water adhering to the space between the electrodes.

This third embodiment provides substantially the same effect as the ones described above and, further, makes it possible to detect water leakage into the tip-section unit 61 regardless of from what direction it has occurred, thereby improving the detection reliability.

As in the above embodiments, it is more effective in this embodiment to cover the humidity sensor 2 with the above-described water-leakage proof member 21 before winding it around the tip-section unit 61. That way, it is possible to detect water leakage before the electronic components inside the unit 61 have been damaged by water intrusion.

Figure 9:
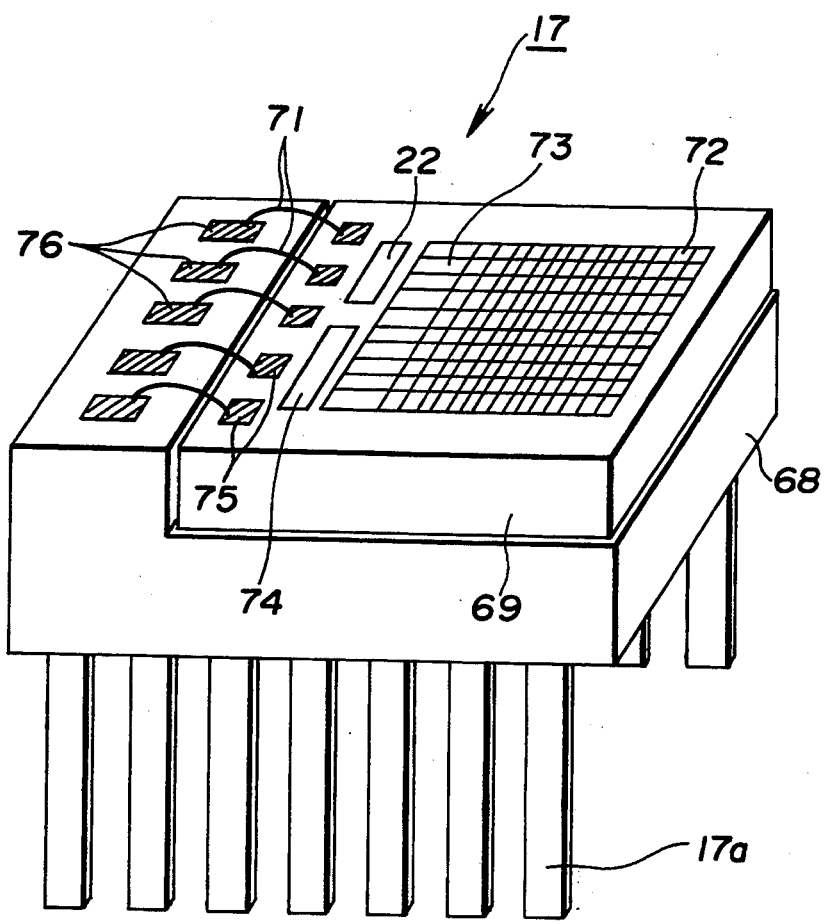
FIG. 9 is an enlarged perspective view showing an SID (solid-state image sensing device) in a fourth embodiment of the present invention.

FIG. 9 is an enlarged perspective view showing an SID 17 according to the fourth embodiment of the present invention. Here, a description of those components of the fourth embodiments which are the same as in the first to third embodiments, described above, will be omitted, and only those points which differ from the other embodiments will be described.

As shown in FIG. 9, the essential section of the SID 17 of the fourth embodiment is composed of a package 68 and a sensor chip 69 arranged thereon. The sensor chip 69 and the package 68 are electrically connected to each other by connecting electrical contacts 75 and 76, respectively provided on them, to each other through bonding wires 71. The output of this SID is emitted from a plurality of lead feet 17a protruding from that surface of the package 68 which is on the opposite side of the sensor chip 69.

When the SID 17 consists, for example, of a CCD, the sensor chip 69 includes an image area 72 consisting of a plurality of photosensitive elements, such as photodiodes, arranged plain-like on the image forming surface, a horizontal CCD register 73 provided on one side of the image area 72, and an output amplifier 74 for voltage-converting photoelectric charge signals, with the plurality of electrical contacts 75 connecting to the above-mentioned bonding wires being arranged at one end of this sensor chip. In this embodiment, a sensor 22 for detecting humidity, etc. is integrally formed on the sensor chip 69, at a position, for example, near the output amplifier 74.

The fourth embodiment, constructed as described above, provides substantially the same effect as the first to third embodiments. Further, since there is no need to form the detection means as a separate unit, the assembly process is simplified and the assembly time is reduced.

Figure 10:
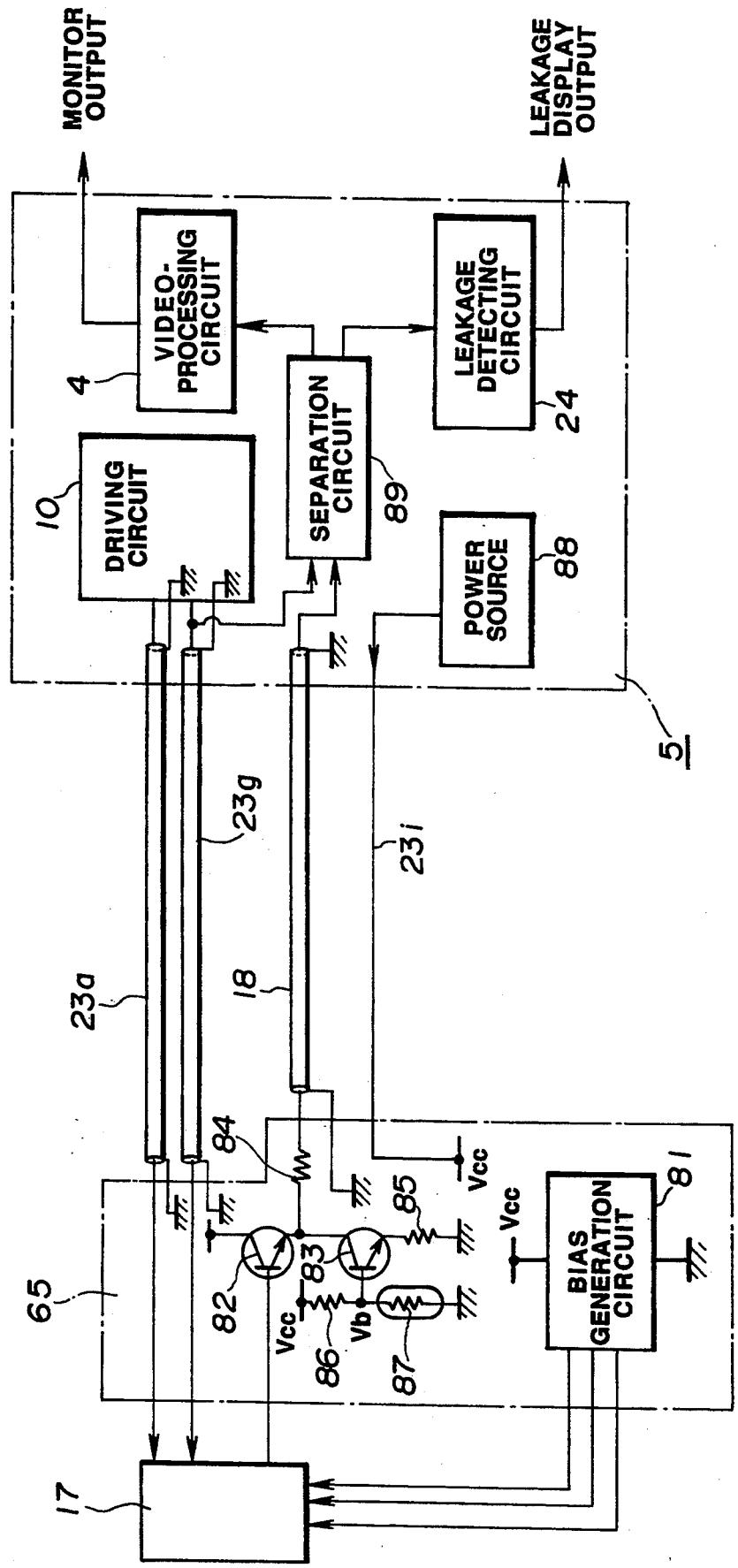
FIG. 10 is a block diagram, partly consisting of a circuit diagram, showing the circuit configuration of an electronic endoscope according to a fifth embodiment of the present invention.

FIG. 10 is a block diagram, partly consisting of a circuit diagram, showing the circuit configuration of an electronic endoscope according to the fifth embodiment of the present invention. In the fifth embodiment, the detection signal from the detection means is transmitted by being superimposed on the SID signal transmission line. A description of those components of the fifth embodiment which are the same as in the first to fourth embodiments will be omitted. The following description of the fifth embodiment will concentrate on what distinguishes it from the others.

As shown in FIG. 10, the output signal of the SID 17 is supplied to a transistor 82 provided within the tip-section IC 65. The emitter of the transistor 82 is connected to a transistor 83, which is designed to operate as a current source. For this purpose, the emitter of the transistor 83 is grounded through a resistor 85 and, at the same time, its base terminal effects voltage division on power-source voltage Vcc by resistors 86 and 87 so as to provide bias voltages. That is, the value of the transistor 83 as a current source is determined by the voltage Vb of the base terminal thereof. This current value is added to the output signal of the SID 17 and transmitted through the cable 18 by way of a matching resistor 84. The resistor 87 constitutes the detection means, such as a humidity sensor, with its resistance value changing in accordance with the detection value. With this construction, two different signals, superimposed one upon the other, are transmitted through the core wire of the cable 18 serving as a signal line which transmits the output signal of the SID 17.

The output signal of the SID 17 is a pulse-like signal generated in response to a pixel drive clock. On the other hand, the output signal of the sensor 87 for detecting humidity, etc. can be treated as a signal indicating a gradual change over time, that is, substantially as a DC component. Thus, the two signals differ in frequency, so that they can be separated from each other by filtering by means of an LPF (low-pass filter), an HPF (high-pass filter) or the like, which forms a separation circuit 89 provided inside the endoscope controller 5. By virtue of this separation circuit 89, the video signal from the SID 17 and the detection signal from the resistor 87 of the humidity sensor, etc. are separated from each other and displayed separately, whereby the detection signal can be visually or audibly displayed in a variable manner based on the gradually changing DC component of the output signal from the resistor 87.

Further, in the fifth embodiment, there is provided a cable 23i which extends, as shown in the drawing, from the endoscope controller 5 to the tip-section IC 65. The cable 23i is a power supply line not consisting of a shielded wire but of a solid wire, supplying the voltage Vcc of a power source 88 provided inside the endoscope controller 5 to the tip-section IC 65 and the SID 17. A bias generating circuit 81 inside the tip-section IC 65 generates the various bias voltages needed for driving the SID 17, such as the SUB voltage and the gate voltages, through voltage division from the voltage Vcc of the power source 88. By thus generating a plurality of divisional voltages in the tip section, the number of cables can be reduced as compared to the case where all the bias voltages are transmitted from the endoscope controller 5. Thus, a further reduction in the diameter of the endoscope is achieved.

Further, due to the fact that the power supply cable 3i consists of a solid wire, it is possible to attain a reduction in impedance with the same diameter as the other coaxial cables 23, and a reduction in diameter with the same level of impedance. The shield portions of the coaxial cables 23a to 23g may serve as the transmission cable for grounding (GND), thereby reducing the diameter of the bundle of cables, facilitating a further reduction in the endoscope diameter.

The fifth embodiment, constructed as described above, provides substantially the same effect as the first to fourth embodiments. Further, due to the generation of the bias voltages in the tip section, the number of cables is reduced. In addition, due to the use of the shield portions of the existing cables as the transmission cable for grounding, a further reduction in the endoscope diameter can be achieved.

Figure 11:
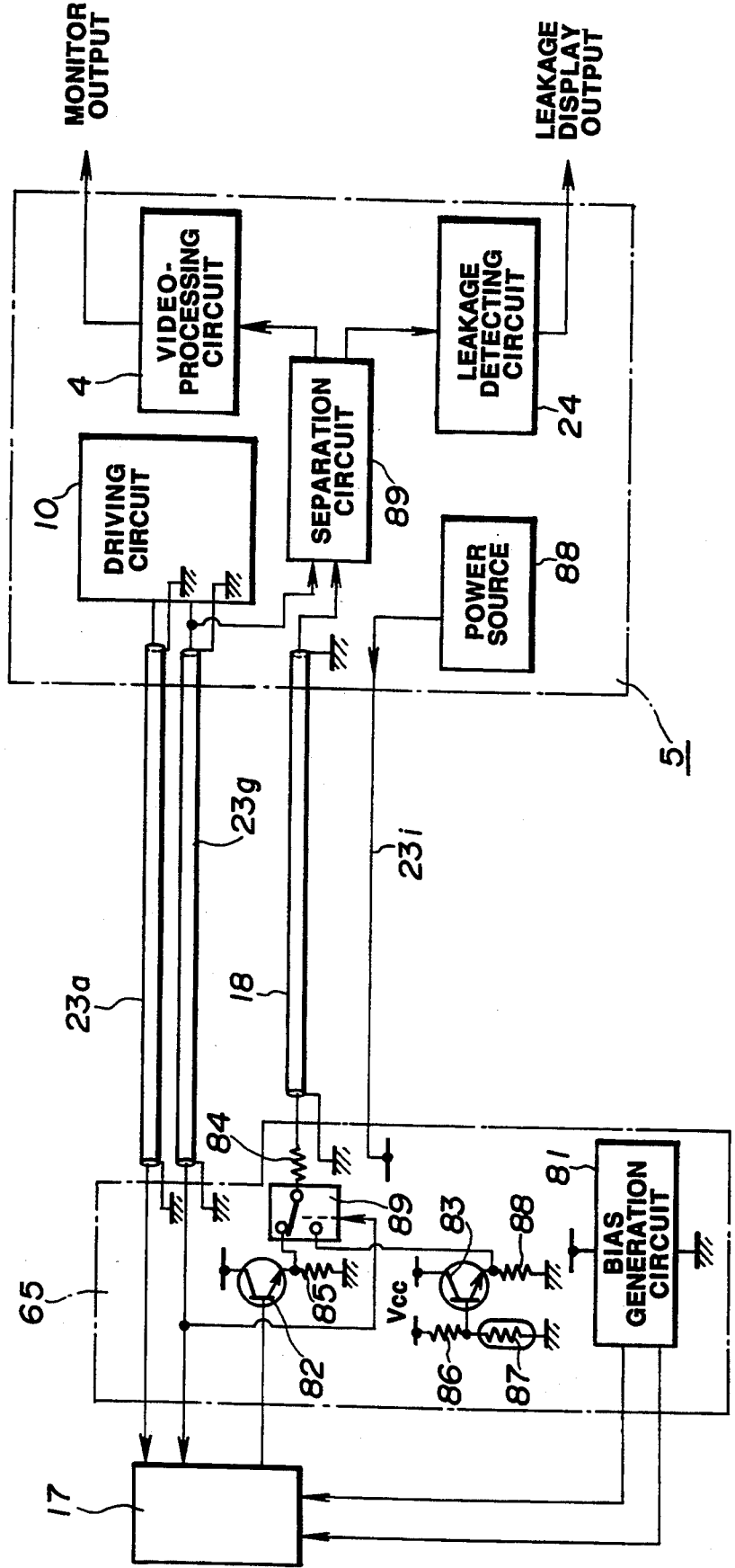
FIG. 11 is a block diagram, partly consisting of a circuit diagram, showing the circuit configuration of an electronic endoscope according to a sixth embodiment of the present invention.

FIG. 11 is a block diagram, partly consisting of a circuit diagram, showing the circuit configuration of an electronic endoscope according to the sixth embodiment of the present invention. In this sixth embodiment, the detection signal from the detection means is time-sequentially transmitted through the SID-signal transmission line, so that this embodiment is substantially the same as the fifth embodiment. Thus, only those points of the sixth embodiment which differ from the fifth embodiment will be described.

As shown in FIG. 11, the output signal from the SID 17 is buffered by an emitter follower formed by the transistor 82 and the resistor 85. An electric potential obtained by effecting voltage division on the power-source voltage Vcc by the resistor 86 and the resistor 87 which constitutes the detection means such as a humidity sensor, is supplied to the base terminal of the transistor 83, the transistor 83 and the resistor 88 forming an emitter follower. Thus, this emitter follower (the transistor 83) emits a buffer output of a signal in accordance with the changes in the resistor 87, which constitutes the detection means such as a humidity sensor.

Of the driving signals supplied to the SID 17, the vertical-register driving signal $\phi V$, etc. are repetitively pulsed at the television horizontal frequency, i.e., 15.734 KHz, and, in many cases, the pulses are within the horizontal-retrace-line period (the blanking period). Within that period, the output signal of the SID 17 is at rest, and is not needed. Therefore, exclusively during this pulse period, the output signal from the SID 17 is time-sequentially switched to the detection signal indicating humidity, etc. by a switching circuit 89, and a plurality of signals are time-sequentially transmitted to the endoscope controller 5 through the same transmission line in the signal cable.

Similarly, in the endoscope controller 5, the separation circuit 89 extracts a signal alternately selecting from the signals in accordance with whether the signal is within or outside the pulse period, thus effecting separation between the signal component from the SID 17 and the signal component from the detection means.

This sixth embodiment provides substantially the same effect as the fifth embodiment described above.

FIG. 12 is a block diagram, partially cut away, showing a rigid endoscope apparatus according to a seventh embodiment of the present invention. The endoscope of the seventh embodiment is a rigid endoscope having a sensor on the surface thereof and adapted to perform sensing on the exterior thereof. Here, a description of those portions of the seventh embodiment which are the same as those of the first to sixth embodiments will be omitted. The following description of the seventh embodiment will concentrate on those points that distinguish it from the other embodiments.

As shown in FIG. 12, the rigid endoscope apparatus 91 of this seventh embodiment has substantially the same construction as the soft endoscope apparatuses described above. A signal cable 95 and a light guide cable 96 can be connected to that side of a rigid endoscope 92 which is nearer to the operator and extended therefrom. Connected to the respective ends of these cables are the endoscope controller 5 and the light-source device 97, thus forming the essential section of the endoscope apparatus.

The rigid endoscope 92 has an objective lens 93 in a tip section 92a thereof, in the focal plane of which lens is arranged the SID 17 for picking up an image of an object. An electric signal photoelectrically converted by the SID 17 is transmitted to the signal lines 18 and 23 by way of a substrate 63. This output signal is supplied through the video-processing circuit 4 to a monitor or the like and observed there.

Further, light emitted from a light source 97a inside the light-source device 97 is transmitted through the light guide 11 consisting of a bundle of fibers or the like, and emitted from an emission end provided in the tip section 92a to illuminate the object.

Provided in the tip section 92a is a sensor 94, such as a pressure sensor, arranged in such a way as to be exposed on the surface of the endoscope, making it possible to detect the condition of the outer environment of the rigid endoscope 92. This pressure sensor consists, for example, of a resistance-wire strain gage, and, as in the above embodiment, its output signal is transmitted through the signal lines 18 and 23 of the SID 17. The reason for thus providing a pressure sensor is to precisely control the pressure inside the abdominal cavity during an operation performed in as state in which the abdomen being inflated by supplying a gas such as $CO_2$ gas into the abdomen by an aeroperitoneal machine (as is particularly needed in an operation using a rigid endoscope) in order to ensure the safety of the organism.

When a pressure sensor is being used as the detection means, as in the above case, it is not absolutely necessary for the sensor to be completely exposed on the surface of the endoscope as shown in FIG. 12. The same effect as in the above case can be obtained, for example, by providing pores on the surface of the endoscope, allowing the sensor to be exposed through these pores.

This seventh embodiment makes it possible to obtain substantially the same effect as the first to sixth embodiments described above even with a rigid endoscope apparatus. Further, due to the provision of the pressure sensor in the tip section, there is no need to increase the diameter of the inserting section of the endoscope, so that the safety of the organism can be secured even in an operation in which gas is supplied into the abdominal cavity.

A desired type of sensor may be selected from the above-mentioned various types of sensor, such as a humidity sensor, pressure sensor, temperature sensor, gas sensor, biosensor, magnetometric sensor and gravity sensor, and used in each of the above-described embodiments.

Further, the present invention is not limited to the use of one type of sensor in an endoscope apparatus. It is of course also possible to construct an endoscope of substantially the same structure having a plurality of types of sensors.

In this invention, it is apparent that a wide range of different working modes can be formed on the basis of this invention without departing from the spirit and scope of the invention. This invention is not restricted by any specific embodiment except as it is limited by the appended claims.

What is claimed is:

1. An electronic endoscope apparatus of the type which includes an inserting section extending from an operating section, said electronic endoscope apparatus comprising:
   detecting means for detecting physical and chemical changes provided at a tip of the inserting section;
   notifying means for notifying the detection results of said detection means;
   image-sensing means provided at the tip of said inserting section for forming an image signal having a blanking period;
   a signal line connected to means and said detecting means for transmitting signals from said detecting means as well as signals from said image-sensing means; and
   a time-sequential signal transmission means for time-sequentially transmitting the signals from said detecting means with respect to the signals from said image-sensing means,
   wherein the signals from said detecting means are transmitted over said signal line during said blanking period.

2. An electronic endoscope apparatus according to claim 1, wherein said detecting means is a humidity detecting means.

3. An electronic endoscope apparatus according to claim 2, wherein said humidity detecting means has two electrodes arranged close to each other.

4. An electronic endoscope apparatus according to claim 2, wherein said image-sensing means is an image-sensing unit, said humidity detecting means being provided in the vicinity of this image-sensing unit.

5. An electronic endoscope apparatus according to claim 1, wherein said detecting means consists of one of the following means: a temperature detecting means, a pressure detecting means, a gas detecting means, a bio detecting means, a magnetic detecting means, or a gravity detecting means.

6. An electronic endoscope apparatus according to claim 1, wherein said time-sequential signal transmission means includes a switching means for time-sequentializing said signals.

7. An electronic endoscope apparatus according to claim 6, further comprising a separation circuit means for separating the time-sequentialized signals from each other.

8. An electronic endoscope apparatus according to claim 1, wherein said detecting means is provided integrally with said image-sensing means.

9. An electronic endoscope apparatus according to claim 1, wherein said notifying means is at least either a visual display means or an auditory notifying means.

* * * * *